United States Patent
Shofner et al.

(10) Patent No.: US 7,345,756 B2
(45) Date of Patent: Mar. 18, 2008

(54) IMAGE-BASED FIBER LENGTH MEASUREMENTS FROM TAPERED BEARDS

(75) Inventors: Frederick M. Shofner, Knoxville, TN (US); Yupeng Zhang, Rensselaer, NY (US); Christopher K. Shofner, Ennis, TX (US)

(73) Assignee: Shofner Engineering Associates, Inc., Knoxville, TN (US)

( * ) Notice: Subject to any disclaimer, the term of this patent is extended or adjusted under 35 U.S.C. 154(b) by 362 days.

(21) Appl. No.: 10/752,873

(22) Filed: Jan. 6, 2004

(65) Prior Publication Data

US 2007/0291270 A1 Dec. 20, 2007

Related U.S. Application Data

(60) Provisional application No. 60/438,681, filed on Jan. 7, 2003.

(51) Int. Cl.
*G01N 21/00* (2006.01)
(52) U.S. Cl. ............................... 356/238.2; 356/238.1; 356/430; 700/142
(58) Field of Classification Search ..................... None
See application file for complete search history.

(56) References Cited

U.S. PATENT DOCUMENTS

| | | | |
|---|---|---|---|
| 2,299,983 A | 10/1942 | Hertel | |
| 2,404,708 A | 7/1946 | Hertel | |
| 3,057,019 A | 10/1962 | Hertel | |
| 4,088,016 A * | 5/1978 | Watson et al. | ................. 73/160 |
| 5,270,787 A | 12/1993 | Shofner et al. | |
| 5,394,480 A * | 2/1995 | Shofner et al. | ........ 250/559.01 |
| 5,491,876 A * | 2/1996 | Shofner et al. | ........... 19/129 R |
| 5,539,515 A * | 7/1996 | Shofner et al. | .......... 356/238.3 |
| 5,639,955 A * | 6/1997 | Anthony | ................... 356/243.1 |
| 5,907,394 A * | 5/1999 | Ghorashi et al. | .......... 356/73.1 |
| 6,052,182 A * | 4/2000 | Irick et al. | ................ 356/238.1 |
| 6,112,131 A * | 8/2000 | Ghorashi et al. | ........... 700/142 |
| 6,314,806 B1 * | 11/2001 | Ghorashi et al. | ............. 73/160 |
| 6,598,267 B2 | 7/2003 | Shofner et al. | |
| 6,735,327 B1 | 5/2004 | Shofner et al. | |
| 2002/0029151 A1 | 3/2002 | Shofner et al. | |

FOREIGN PATENT DOCUMENTS

WO WO 01/20321 A2 3/2001

OTHER PUBLICATIONS

F.M. Shofner and C.K. Shofner, "Cotton Classing in the New Millennium," Invited Paper for 25th International Cotton Conference, Bremen, Germany Mar. 1-4, 2000.

* cited by examiner

*Primary Examiner*—Gregory J. Toatley, Jr.
*Assistant Examiner*—Juan D. Valentin, II
(74) *Attorney, Agent, or Firm*—Carter & Schnedler, P.A.

(57) ABSTRACT

An image-based method and corresponding apparatus for measuring, in scientifically basic terms, the complete fiber length distribution from a tapered beard. The method may be referred to as length by image analysis ($L_i$).

13 Claims, 11 Drawing Sheets

000
IMAGE-BASED FIBER LENGTH MEASUREMENTS FROM TAPERED BEARDS

CROSS-REFERENCE TO RELATED APPLICATION

The benefit of U.S. provisional patent application Ser. No. 60/438,681, filed Jan. 7, 2003, is claimed.

BACKGROUND OF THE INVENTION

Fiber length measurements from tapered beards were disclosed by Hertel in the 1940's. Hertel employed the term "amount" (A) to refer to the amount (that is, number or linear density) of fibers in tapered beards and developed what he termed "fibrograms," which are plots of "amount" as a function of distance from a needle sampler. Hertel worked out the theory for analyzing fibrograms and developed apparatus and methods for length measurements from the 1930s to the 1950s. In particular, Hertel disclosed the determination of a length-distribution curve based on optical analysis. See, as examples, Hertel U.S. Pat. Nos. 2,299,983, 2,404,708 and 3,057,019. For convenience, we refer herein to the result of this measurement method, as well as the method itself, as $L_O$, meaning length by optical analysis.

A needle sampler for forming tapered beards and employing rotary motions is disclosed in Shofner et al U.S. Pat. No. 6,598,267, titled "Fiber Length and Strength Measurement System," the entire disclosure of which is hereby expressly incorporated by reference. The disclosed apparatus uses optical extinction, and may also be referred to as an $L_O$ method. In addition, the apparatus disclosed in U.S. Pat. No. 6,598,267 employs air flow resistance to measure the amount versus distance response. We refer herein to length measured by air flow resistance, as well as the method, as $L_a$.

The terminologies complete fiber length distribution, fiber length histogram, and fiber length probability density function (PDF) are interchangeably used herein and in the literature on fiber length measurements.

Cotton fiber length measurements (Classer's Staple, 2.5% Span, Upper Half Mean, etc., and Short Fiber Content, etc.) are among the most important descriptors of fiber quality. They strongly correlate with spinning process costs and yarn and fabric qualities. Accordingly, these and related data products strongly impact commercial market values of cotton. It is important that the measurement, or classification, of the qualities be correct, widely understood, and accepted for commercial trading by all parties concerned.

The market has historically caused producers to favor varieties having greater Long Fiber Content (LFC) when all other things, notably pounds per acre yield, are comparable. Reasonably satisfactory LFC measurements are available and widely used in commerce. On the other hand, satisfactory Short Fiber Content (SFC) measurements are not available, despite numerous complaints, primarily from parties in the mill, merchandizing and research segments, which refer to the "rising short fiber content" problem. Current market forces are increasingly causing producers and ginners to favor processing equipment and methods which minimize damage and preserve the length qualities of the fibers, thus minimizing SFC. Accordingly, correct measures of SFC are needed.

The best measure of fiber damage, both in the gins and in the mills, and of spinning performance in the mills, is SFC, either by number or by weight. Only with correct and widely accepted SFC data can producers and designers and operators of processing machinery evaluate the quality of their work and, thereby, realize the financial incentives to improve.

Commercial market forces which are driving all parties concerned to higher (or at least stable) LFCs and lower SFCs are thus also driving the needs for correct, commercially-useful measurements. This means scientifically basic, accurate, precise, rapid and cost-effective measurement of both long fiber content LFC and short fiber content SFC. It follows further that the most basic and best methods provide direct measurement of the complete fiber length distribution, or probability density function (PDF), since all fiber length data products can be derived therefrom.

Current High Volume Instruments (HVI) provide LFC data products, such as Upper Half Mean Length (UHM) or Mean Length (ML), satisfactorily for commercial purposes, along with other fiber quality measurements such as strength (or tenacity), micronaire, color and trash. Such instruments are manufactured by Uster Technologies, Knoxville, Tenn.; Premier Technologies, Coimbatore, India; Lintronics, Haifa, Israel; and Schaffner Technologies, Knoxville, Tenn., with which the present inventors are associated. Current HVI methods however do not provide adequate measurements of the shortest fibers, for several fundamental reasons relating to both sample preparation and tapered beard "amount" (A) measurement. Consequently, current HVI does not provide the complete fiber length distribution and only provides inferential measures of SFC.

The Advanced Fiber Information System (AFIS) also manufactured by Uster Technologies (for an example see the disclosure of Shofner et al U.S. Pat. No. 5,270,787 titled "Electro-Optical Methods and Apparatus for High Speed, Multivariate Measurement Of Individual Entities In Fiber Or Other Samples"), and Suter-Webb array, methods can provide complete fiber length distributions or PDFs. These methods are known to be too expensive, imprecise, or slow for high volume testing. It is also known that AFIS, as a consequence of its rather aggressive opening to produce single fibers, breaks fibers, thus leading to increased SFC and decreased LFC, thus biasing the length data products.

Since new length methods are needed, primarily for commercial trade, it follows that the most preferable methods would be also be compatible with next generation HVI, along with improvements in other fiber quality measurements, such as strength, micronaire, color and trash.

SUMMARY OF THE INVENTION

In an exemplary embodiment, apparatus for fiber length measurements from a tapered beard attached to a fiber sampler, includes a rectangular channel into which a tapered beard is drawn by a gas flow through the channel. The channel has two opposed major sides corresponding to channel width and length, and two opposed minor sides corresponding to channel height and length. One of said major sides takes the form of a transparent window, and an optical imaging device views the tapered beard through the transparent window for acquiring a two dimensional image of the tapered beard. A digital computer is connected to an output of the optical imaging device for storing two-dimensional image data and determining fiber amount as a function of one-dimensional distance x from the fiber sampler by averaging across the width of the tapered beard as imaged.

In another embodiment, apparatus for fiber length measurements from a tapered beard attached to a fiber sampler is provided. The apparatus includes a scanner intended for scanning documents positioned with reference to the tapered beard for acquiring a two dimensional image of the tapered beard.

In yet another embodiment, a method for image based length measurement is provided. The method includes acquiring a two-dimensional digital image of a tapered beard of fibers, which beard has a length; employing a computer to analyze the digital image to determine fiber amount as a function of one-dimensional distance along the length of the tapered beard by averaging across the width of the tapered beard as imaged; and analyzing the determined fiber amount as a function of distance to produce a fiber length distribution.

In still another embodiment, a method for calibrating length measurement systems providing calibrated probability density functions (PDFs) for unknown tapered beards includes the steps of forming a tapered beard subsample from a bulk sample of at least one sample of known, monolength staple fibers, the fibers of the bulk sample having diameter and surface properties similar to those of subsequent samples under test having unknown length distributions; measuring the uncalibrated amount versus distance response for each such monolength group; developing correction functions from each such monolength sample to provide calibrated amount versus distance distances for said monolength fibers; storing said calibration functions and interpolations thereof in a computer memory; forming a tapered beard subsample of unknown length fibers and measuring the uncalibrated amount versus distance response; correcting the amount versus distance response for said unknown tapered beard to produce a calibrated amount versus distance response; determining the second derivative of said calibrated amount versus distance response for said unknown tapered beards; normalizing and filtering the second derivative to produce a calibrated PDF for the unknown subsample; calculating from said calibrated PDF any length data products desired.

DETAILED DESCRIPTION

Disclosed herein is an image-based method and corresponding apparatus for measuring length properties of staple and other textile fibers. More particularly, embodiments of the invention determine, from a tapered beard, and in scientifically basic terms, the complete fiber length distribution or probability density functions (PDFs) and data products determined therefrom. The method may be referred to as length by image analysis ($L_i$). Fiber "amount" (A) as determined by the image-based method and corresponding apparatus disclosed herein is designated $A_i$ (amount by imaging), and closely corresponds to Hertells "amount." The precision, accuracy, speed and cost of both LFC and SFC data products derived equal or exceed those of the best available prior art technologies. Traditional procedures for determination of length properties are also provided.

The LFC data products provided by the subject $L_i$ method are precisely those with which the industry is familiar and upon which commercial trade is based: Upper Half Mean Length (UHM), Mean Length (ML), and Length Uniformity=ML/UHM. Classer's Staple, in 32nds of an inch, is calculated as 32×UHM. SFC is also traditional: percent of fiber weight associated with fibers having lengths<0.5 inch. All of these data products are on a weight basis. Short Fiber Content by number, $SFC_n$, is also used. A basic data product of embodiments of the invention is $PDF_n$, from which $PDF_w$ and all other by-number or by-weight data products are derived. Data products herein are understood to be on a weight basis unless indicated otherwise. The by-weight data products provided by embodiments of the subject invention are thus traditional in definition and level. However, they are more accurate and precise than currently available and have other merits, notably provision of high quality color images for inspection.

Figure 1:
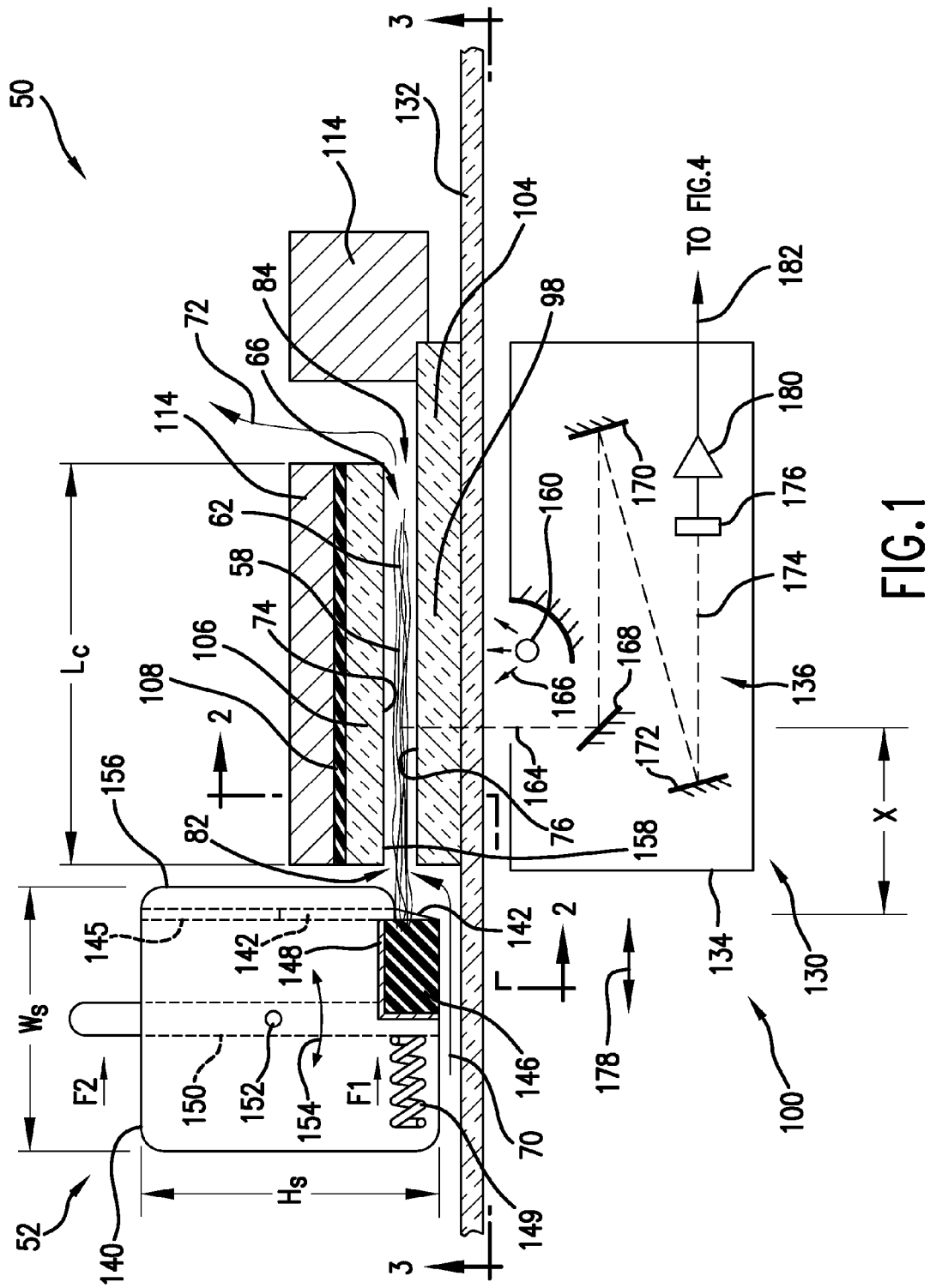
FIG. 1 is a somewhat schematic side view, partially in section, of apparatus embodying the invention.
Figure 2:
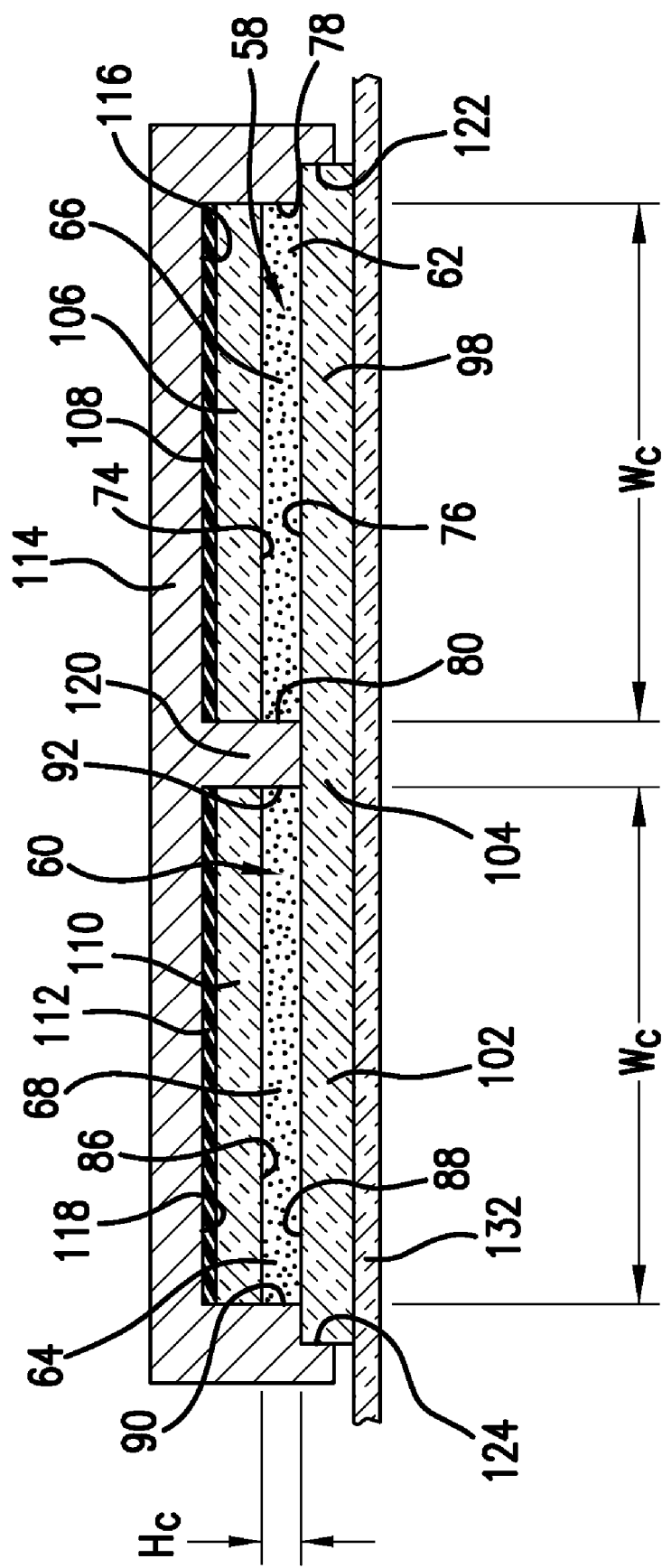
FIG. 2 is a cross-sectional view taken on line 2-2 of FIG. 1.
Figure 3:
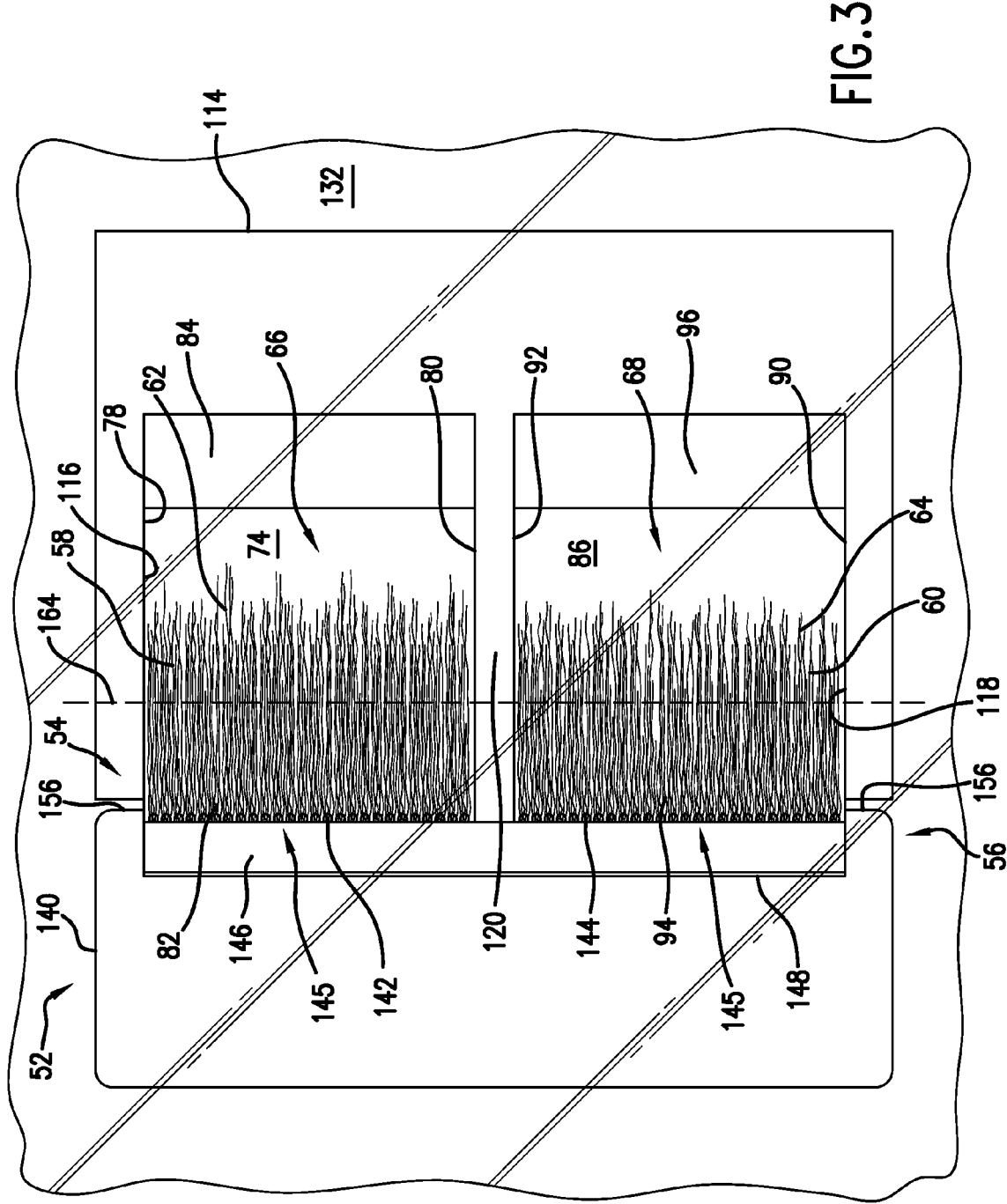
FIG. 3 is a view looking out through the glass of a scanner included in the apparatus of FIG. 1 (upwardly in the orientation of FIGS. 1 and 2) taken on line 3-3 of FIG. 1, showing two tapered beards attached to respective sections of a needle sampler including respective sets of closely-spaced needles.

Referring now to FIGS. 1, 2 and 3, an image-based length measurement apparatus 50 includes a dual-beard needle sampler 52 having two sides 54 and 56 or sections 54 and 56 (FIG. 3). The needle sampler 52 is similar to the needle sampler disclosed in the above-incorporated Shofner et al U.S. Pat. No. 6,598,267. The needle sampler sides 54 and 56 hold respective tapered beards 58 and 60 each comprising a multiplicity of fibers 62 and 64. The tapered beards 58 and 60 are drawn into respective rectangular channels 66 and 68 by gas flow through the channels 66 and 68, as indicated by gas flow arrows 70 and 72 for representative channel 66. Arrow 72 in particular represents suction gas flow. Gas flows through each of the channels 66 and 68 at a rate of approximately 0.25 m³/sec. Although the channels 66 and 68 are shown as horizontal channels, that is for convenience of illustration and description only; in apparatus embodying the invention a more space-efficient arrangement may have the channels 66 and 68 oriented vertically (rotated 90° with reference to the FIG. 1 orientation). There are two needle sampler sides 54 and 56 and two tapered beards 58 and 60 drawn into two channels 66 and 68 because separate fiber samples are conventionally taken from two opposed sides of a bale of cotton (not shown).

The channels 66 and 68 are essentially identical, each having a typical channel height $H_C$ of approximately 0.08 inch (2 mm), a typical channel width $W_C$ of approximately 4.0 inches (100 mm), and a typical channel length $L_C$ (parallel to the fibers 62 and 64 of the tapered beards 58 and 60) of approximately 2.0 inches (50 mm). Representative channel 66 has two opposed major sides 74 and 76 corresponding to channel width $W_C$ and length $L_C$, and two opposed minor sides 78 and 80 corresponding to channel height $H_C$ and length $L_C$. Representative channel 66 has an inlet 82 and an outlet 84 corresponding to channel height $H_C$ and width $W_C$. Channel 68 likewise has two opposed major sides 86 and 88 corresponding to channel width $W_C$ and length $L_C$, two opposed minor sides 90 and 92 corresponding to channel height $H_C$ and length $L_C$, as well as an inlet 94 and an outlet 96 each corresponding to channel height $H_C$ and width $W_C$.

Major side 76 of channel 66 (the lower side in the orientation of FIGS. 1 and 2) comprises a lower (again, in the orientation of FIGS. 1 and 2) transparent window 98 made of glass through which the tapered beard 58 is viewed by an optical imaging device, generally designated 100, and major side 88 of channel 68 (the lower side in the orientation of FIGS. 1 and 2) comprises a lower (in the orientation of FIGS. 1 and 2) transparent window 102 made of glass through which the tapered beard 60 is viewed by the optical imaging device 100. In the illustrated embodiment, the windows 98 and 102 actually comprise a single sheet or plate of glass 104. The optical imaging device 100 acquires a two-dimensional image of each of the tapered beards 58 and 60 as is described in greater detail hereinbelow, and preferably in color.

The major sides 74 and 86 of the channels 66 and 68, respectively, (the upper sides in the orientation of FIGS. 1 and 2) each comprise a low reflectance black background. More particularly, the major side 74 of channel 66 is defined by an upper piece of glass 106 backed by a coating 108 of black silicon rubber, which, in addition to its light-absorbing function, serves as an adhesive. Likewise, the major side 86 of channel 68 is defined by an upper piece of glass 110 also backed by a coating 112 of black silicon rubber serving both light-absorbing and adhesive functions. Supporting structure includes an aluminum body 114 having a pair of rectangular recesses 116 and 118 separated by a partition 120, as well as a pair of side recesses 122 and 124. The upper piece of glass 106 is secured within the rectangular recess 116 by the black silicon rubber 108, and the upper piece of glass 110 is secured within the rectangular recess 118 by the black silicon rubber 112. The sheet of glass 104 common to the windows 96 and 102 is secured within the side recesses 122 and 124 by adhesive (not shown).

In the illustrated embodiment the optical imaging device 100 comprises a high quality color scanner, generally designated 130, intended for scanning documents, and described in greater detail hereinbelow. The high quality color scanner 130 includes a glass window 132, as well as scanner components generally designated 134, which may also be referred to as a scanner head 134, in turn including an optical imaging system 136. However, the scanner 130 is representative only of the optical imaging device 100, and the optical imaging device 100 may comprise a digital camera, as an example. Moreover, the illustrated optical imaging device 100 operates in reflection mode, viewing the generally white tapered beards 58 and 60 against the black backgrounds 74 and 86. However, a two-dimensional optical imaging device 100 operating in transmission mode may as well be employed, or even a combination of reflection and transmission modes.

The invention may also be embodied in a stationary scanner head, in combination with movable sampler, which likewise provides relative motion between tapered beards 58, 60 and spatially and spectrally resolved scan line 164 to produce a digital image. In FIG. 1, sampler 52 may move horizontally or vertically to withdraw beards 58 and 60 from channels 66 and 68.

The sheet of glass 104 common to the windows 98 and 102 is positioned over the glass window 132 of the scanner 130 so that the scanner components 134 view the tapered beards 58 and 60 against the black backgrounds 74 and 86. Even though the tapered beards 58 and 60 are not positioned directly on the scanner glass 132, the optical imaging system 136 has a depth of field sufficient to produce quality images. But if the images are blurred due to being out of focus, the scanner optical system 136 is simply refocused or realigned.

With particular reference to FIGS. 1 and 3, the needle sampler 52 comprises a body 140 having a typical sampler body 140 width $W_S$ of 1.0 inch and a height $H_S$ of 1.5 inches. Two sets of hardened steel needles 142 and 144 are pressed and/or glued into holes 145 in the sampler body 140. Alternatively, the hardened steel needles 142 and 144 may be silver soldered onto a brass plate (not shown), which is in turn attached by screws (not shown) to needle sampler 52 body 140. In the view of FIG. 3, pointed ends of the needles 142 and 144 are visible, along with the tapered beards 58 and 60 retained on and extending from the needles 142 and 144.

More particularly, the tapered beards 58 and 60 are retained on the needles 142 and 144 by a piece of locking elastomer 146. Locking elastomer 146 is preferably 0.25× 0.25 inch Buna N material mounted in a holder 148. The holder 148 in turn is pressed against needles 142,144 by springs 149 and is actuated by a lever 150 or arm 150 which rotates slightly on an axis 152 as indicated by arrow 154 to open and close a locking mechanism enabled by springs 149. Approximately forty pounds of closing force F1 between the elastomer 146 and rows of needles 142 and 144 is provided by springs 149, for each side 54,56 of sampler 52. This force Fa is adequate for each of the two four-inch-wide needle sampler 52 sides 54,56 having thirty-five 0.063 inch diameter needles 142 and 144 spaced 0.125 inch centerline to centerline. Other needle diameters and centerline spacing may be used, including 0.04 inch (~1 mm) and 0.08 inch (~2 mm), respectively. Spring 149 closing force F1 is opposed for opening or unlocking the beard by application of external force F2 to upper end of arm 150.

FIG. 1 is not drawn entirely to scale. The distance from an imaginary line drawn through the centers of the needles 142 and 144 and the side 156 of the needle sampler body 140 is 0.053 inch. The distance from the side 156 of the needle sampler body 140 to the beginning 158 of low reflectance surface 74 or 86 is 0.01 inch. Adding these two distances, the distance from an imaginary line drawn through the centers of the needles 142 and 144 and the beginning 158 of low reflectance surface 74 or 86 is 0.063 inch.

It will be appreciated that other needle diameters, spacings, materials of construction and the like may be employed in other embodiments of the invention.

As is seen in FIG. 3, the tapered beards 58 and 60 are produced by relatively closely-spaced needle sets 142 and 144. Alternatively, and as disclosed in the above-incorporated Shofner et al U.S. Pat. No. 6,598,267, in other embodiments of the invention, relatively widely-spaced needles (not shown) may be employed to produce two multiplicities of single needle, tapered beards (not shown) respectively drawn into the channels 66 and 68.

During operation of either manual or automatic embodiments of the invention, in a conventional manner two adjacent bulk samples of fibers (not shown) are pressed onto one side of a perforated plate (not shown) so that there are protrusions of fibers (not shown) on the other side of the perforated plate pressed through apertures in the perforated plate. Needle sampler 52 is opened, meaning that the elastomer 146 is rotated away from needle sets 142, 144 by the action of external force F2, and thus engages the protrusions of fibers after moving by at least one, typically five, and maximally by twenty ten rows of such protrusions. Typically five rows of 0.63×0.75 inch elongated apertures in 0.100 inch thick steel plates are adequate. The elongated apertures are chamfered and polished and are in a staggered pattern with centerline spacings of typically 0.75 and 1.0 inches. The bulk samples of fibers are pressed against the perforated plate with a force of about 0.5 pound per square inch, typically.

After the open needle sampler 52 is passed near the perforated plate such that subsamples are collected from the bulk samples, the sampler 52 is locked. In particular, the locking elastomer 146 (FIGS. 1 and 2) is pressed against the needles 142 and 144, by releasing, or in some cases, reversing, external force F2. After conventional combing and brushing steps to prepare the final tapered beards 58 and 60, the sampler 52 with attached tapered beards 58 and 60 is transported to the position shown in FIGS. 1-3.

Scanner 130 more particularly is preferably a color scanner operating at 50 to 1200 dots per inch (dpi) resolution, with an 8.5×11 inch scan area, and with eight or more bits per color of "pixel depth." The scanner components 134 include a linear light source 160, such as a lamp 160, the intensity of which is controlled in a manner conventional in color scanners. The light source 160 is backed by a concave mirror 162 and illuminates the tapered beards 58 and 60, at least along a highly resolved scan line 164, as indicated by rays 166. For compactness, the optical imaging system 136 includes a folded mirror system comprising mirrors 168, 170 and 172 which direct a representative ray 174 into a high density linear light detection device 176, such as a CCD array 176, as the scanner components 134 (or scanner head 134), and therefore the highly resolved scan line 164, physically move from left to right (in the orientation of FIG. 1) in a conventional manner as indicated by arrow 178, driven by a motor (not shown). The CCD array 176 includes a multiplicity (thousands) of individual detector elements, enabling high spatial resolution or, stated alternatively, small picture elements or pixels. Moreover, there are red-, green- and blue-spectral sensitive detector elements, thus enabling spectral resolution. In FIG. 3, the distance of the scan line 164 from the needles 142 and 144, and in particular from an imaginary line drawn through the centers of the needles 142 and 144, is indicated as distance x. Spectrally- and spatially-resolved light components detected by the CCD array 176 are digitized by an A/D converter and associated electronics, collectively designated 180, which produce an output on representative signal line 182 connected to a digital computer system 184 (FIG. 4) for image processing as described hereinbelow.

Figure 4:
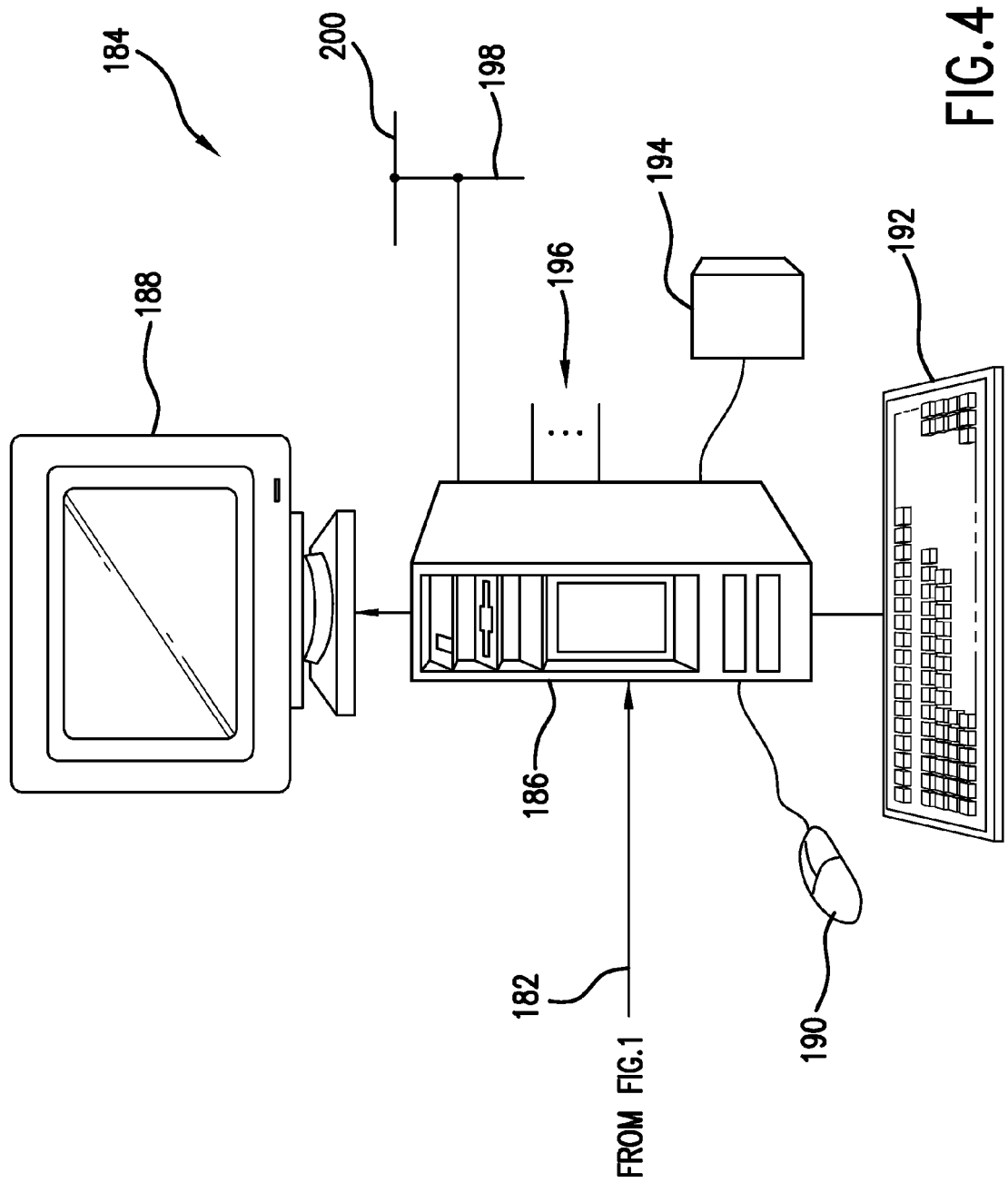
FIG. 4 represents a computer system connected to an output of the scanner included in the apparatus of FIG. 1.

FIG. 4 thus generally shows the digital computer system 184 including a CPU 186, display 188, mouse 190, keyboard 192, storage devices 194, and other peripherals 196. Display 188 may be a touch screen. Computer system 184 is connected to a local area network 198, as well as to internet 200.

Figure 5:
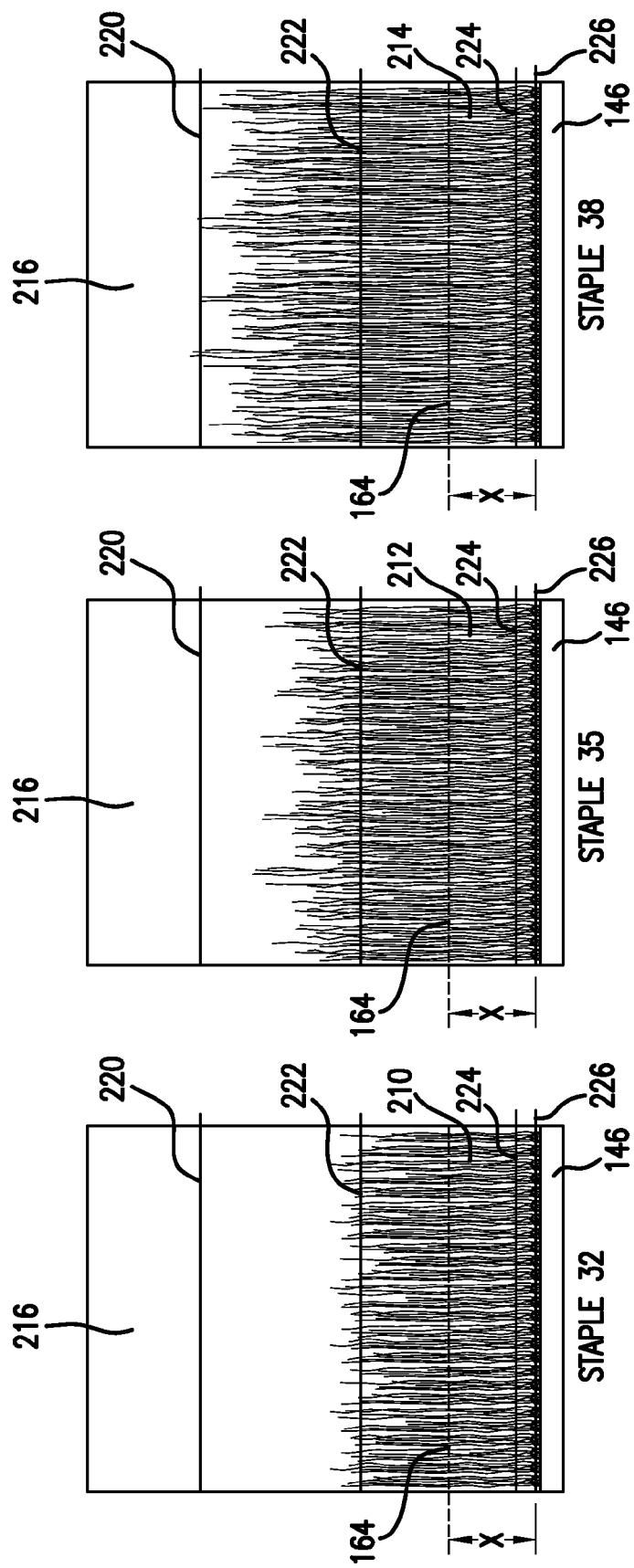
FIGS. 5A, 5B and 5C are views similar to FIG. 3 representing actual images of beards for three Staple Standards.

FIGS. 5A, 5B and 5C are side-by-side illustrator's renditions of actual images of three tapered beards 210, 212 and 214 from one side of the needle sampler 52, obtained from three separate tests. FIGS. 5A, 5B and 5C are drawn from inspection of color-positive images of beards formed from three different staple length cottons, in particular USDA Staple standards Staple 32, Staple 35 and Staple 38. "Staple 32" means the longest fibers are 32/32 inch (=1.0 inch) long; "Staple 35" means the longest fibers are 35/32 inches long; and "Staple 38" means the longest fibers are 38/32 inches long. The fiber length distributions are polydisperse or polylength. In each case, the tapered beard is from one side of the needle sampler 52 having closely-spaced needles 142 or 144, with the tapered beard attached or locked thereto, and drawn into channel 66 or 68. It will be appreciated that FIGS. 5A, 5B and 5C are negative renditions, as the original images, like the objects (beards), have color intensities rising from low values, on a black background 216, to high color intensity values as an increasing number of fibers is seen in moving from upper portions of the background region 216 (in the orientation of FIGS. 5A, 5B and 5C), where there are no fibers, to thick ends of tapered beards 210. 212 and 214, where the maximum number of fibers occurs, around needles 142 and 144.

Four horizontal reference lines or stripes 220, 222, 224 and 226 are superimposed in each of FIGS. 5A, 5B and 5C. Line 220 is a 1.0-inch reference. Line 222 is a 0.5-inch reference. Line 224 is the starting line for image analysis, discussed hereinbelow, and is near, but not necessarily coincident with, the beginning 158 (FIG. 1) of low reflectance surface 74 or 86. Reference line 226 corresponds to zero length, or x=0, in the plane of centerlines of the sampling needles 142 and 144, which plane is perpendicular to the scanner glass 132.

Each tapered beard image, after analysis, can be compressed and archived to a computer database. Each tapered beard image may be made part of the sell-buy negotiations or trading record. Tapered beard images may be accessed and communicated over the internet for remote inspection or even analysis in a manner related to what is disclosed in Shofner et al Patent Application Publication No. US 2002/0029151 A1 titled "System and Method for Marketing Cotton.

In one particular form of data presentation (not shown), a sample under test is presented in a manner similar to FIGS. 5A, 5B and 5C, but with closer spacing, between samples whose length properties are known. In other words, the image of the sample under test is in the position of FIG. 5B, and images of known references are in the positions of FIGS. 5A and 5C, closely spaced to FIG. 5B. This is a powerful tool for training, for communications between specialists, and for arbitration.

Disclosed and discussed next is the manner in which tapered beard amount-by-imaging $A_i$ as a function of x data are determined, followed by the manner in which useful and conventional length data products, and particularly the length probability distribution functions (PDFs) are determined. Also disclosed is calibration for useful and known length data products, as well as for the PDF itself.

The spectrally- and spatially-resolved light components detected by the CCD array 176 and digitized by A/D converter and associated electronics 180 to produce an output on signal line 182 are, as noted above, from scan line 164. We have discovered that these spectrally- and spatially-resolved light reflection (or, in other embodiments, transmission) components, above background, when averaged (by software executing in CPU 186) along the scan line 164 across the widths of the beards 58 and 60 to produce amount $A_i$ for each resolved distance x, are remarkably useful analogs of Hertel's "amount" (A) or number of fibers in tapered beards 58 and 60. The digitized intensity signals from eight-bit outputs of A/D converter 180 range, for the color green, from about 20 counts for background to about 220 counts where the maximum number of fibers occurs, near the row of needles 142 and 144. Other digital resolutions and colors may be used.

Of particular usefulness is the inherent spatial resolution provided by the optical imaging device 100. Resolutions from 50 to 1200 dots per inch (dpi) are achieved with current technology scanners and cameras, for each of red, green and blue colors. Typical resolutions employed in the practice of the invention are 150 dpi; higher resolutions yield more faithful images, but larger data files for processing. Each application dictates the best compromise between resolution and processing time. At 150 dpi, image file size is of the order of Megabytes.

As noted above, the detected signal amount from A/D converter 180, for each color and each pixel of resolution, when averaged (by software executing in CPU 186) along the scan line 164 across the widths of the beards 58 and 60 to produce amount $A_i$ for each resolved distance x, is a useful indication of the number of fibers in the tapered beard at distance x. For fiber samples whose average linear densities are reasonably constant, it follows that these signals are similarly useful indications of the linear densities of beards 58 and 60 at each distance x along the highly resolved scan line 164.

One measure of linear density (weight per unit length) that is frequently used for textile fiber characterization is the quantity tex, defined as the weight in grams of 1000 meters of fibers. Another measure is micrograms per inch. The linear densities of cotton fibers are typically in the range of 100 to 200 millitex or, roughly, 2.5 to 5 µg/inch. (It may be noted that the latter values have a historical basis in the measurement of Micronaire. The dimensionless values of Micronaire replaced the strict linear density specification of µg/inch when it was discovered that the cross sectional characteristics of fiber influence the air flow permeability measurements of Micronaire. Micronaire values are widely used for trade, and Micronaire is frequently misunderstood as being the same as linear density, which it is not.) In any event, the detected signals from A/D converter 180, when averaged (by software executing in CPU 186) along the scan line 164 across the widths of the beards 58 and 60 for each resolved distance x, are similarly useful indications of the linear density or tex of the beards 58 and 60 at each distance x along the highly resolved scan line 164. Thus, embodiments of the invention provide for amount, in number of fibers or in linear densities of tapered beards, as a function of distance x. Thus spatially and spectrally resolved amount $A_i$, as a function of distance x along the beards 58 and 60 is a fundamentally important measure of the properties of the beards 58 and 60.

Faithful analogs of amount (A) may also be produced with transmission or extinction mode optics (not shown). It is equally appropriate to refer to a transmission image, in analogy with a photographic transparency, as it is to the more common reflection image. Image-based length methods and apparatus embodying the invention may employ include both reflection images, transmission images, or both. In some cases it is advantageous to combine reflection and transmission signals.

Figure 6:
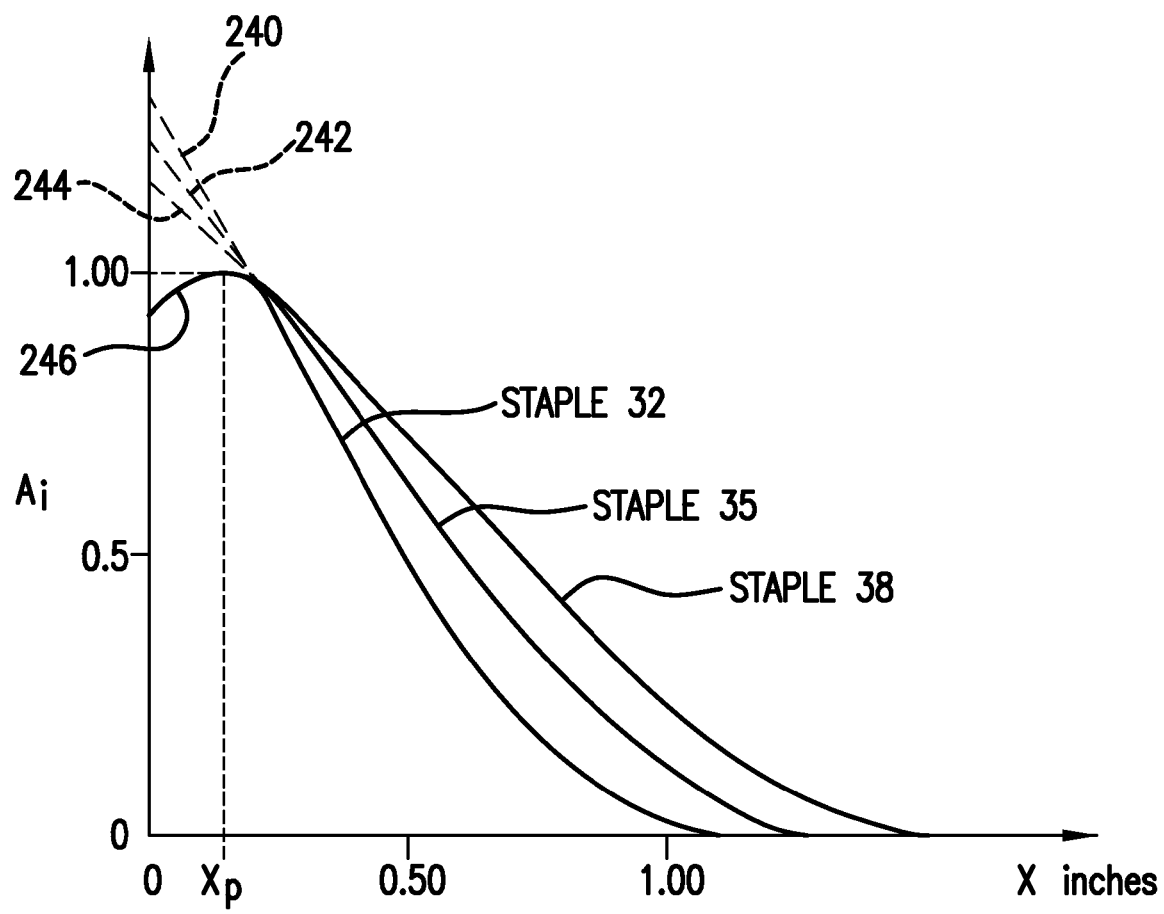
FIG. 6 shows plots of $A_i$ (amount by imaging) as a function of x based on the Staple 32, Staple 35 and Staple 38 cottons images represented in FIGS. 5A, 5B and 5C.

FIG. 6 shows plots of $A_i$ as a function of x based on the Staple 32, Staple 35 and Staple 38 cottons image represented in FIGS. 5A, 5B and 5C, as indicated. The FIG. 6 plots may also be referred to as fibrograms. These image-based fibrograms, or plots of amount $A_i$ vs distance x, are produced by plotting $A_i$ as a function of displacement of the scanner head 134 from the needles 142 and 144 and, more particularly, distance along the lengths of the tapered beards 58 and 60. $A_i$ is normalized to unity at $x_p$, a peak value which typically occurs when the scan line 164 approaches the beginning 158 of the low reflectance surface 74 or 86 (FIGS. 1 and 3). There are several practical reasons for these peaks, including decrease in background, holes or gaps in the beards 58 and 60 associated with the needles 142 and 144, and different orientations or presentations of the beards 58 and 60 outside the rectangular channels 66 and 68. If the apparatus 50 were ideally responsive only to the number of fibers in the tapered beards 58 and 60, then the $A_i$ vs x curve would extrapolate to x=0 generally along dashed lines 240, 242 and 244 in FIG. 6. These extrapolations are in the limit straight lines; more rigorously, they are curves with positive upward concavity. This non-ideal response is further discussed hereinbelow in the context of in the disclosures herein of PDF calibrations.

Analysis of this amount versus distance ($A_i$ versus x) by either traditional methods or by new methods disclosed hereinbelow yield LFC and SFC data products. The methods of analysis disclosed herein enable provision of a calibrated, complete fiber length distribution or probability density function (PDF), a significant aspect of some embodiments of the invention. This means that all LFC and SFC data products can be directly derived from the PDFs, without reference to calibration materials except for calibrating the basic instrument response. This rigorous calibration will be appreciated as a significant improvement provided by the invention.

Because the $A_i$ is a faithful analog of Hertel's "amount," it follows that the beards may be tested advantageously for strength, i.e., tenacity, and elongation. This is fundamentally important for use with next generation HVI.

Referring again to FIG. 6, some other major features (besides the peaks) may be noted. First, as the staple fiber length increases (32/32 inch, 35/32 inches and 38/32 inches), the fibrograms shift to the right. Second, as staple fiber length increases, the curvature of the fibrograms decreases. This is because, typically, longer staple fiber distributions have lower short fiber content. Representative data are SFC=15%, 10% and 7% for Staple 32, Staple 35, and Staple 38, respectively, and as reported hereinbelow.

The $A_i$ vs x fibrograms of FIG. 6 are for polydisperse or polylength fiber length distributions. Thus it is well known that natural fibers such as cotton or wool have a wide range of lengths in the bulk samples. However, for purposes of analysis and in the context of the disclosure of the methods herein, it is useful to refer to the situation where all fibers are of the same length. The disclosure to follow is directed toward PDFs by number but it can be appreciated that the concepts similarly apply to rigorous calibrations to PDFs by weight, starting with amounts Ai in terms of linear density or tex.

Figure 7A:
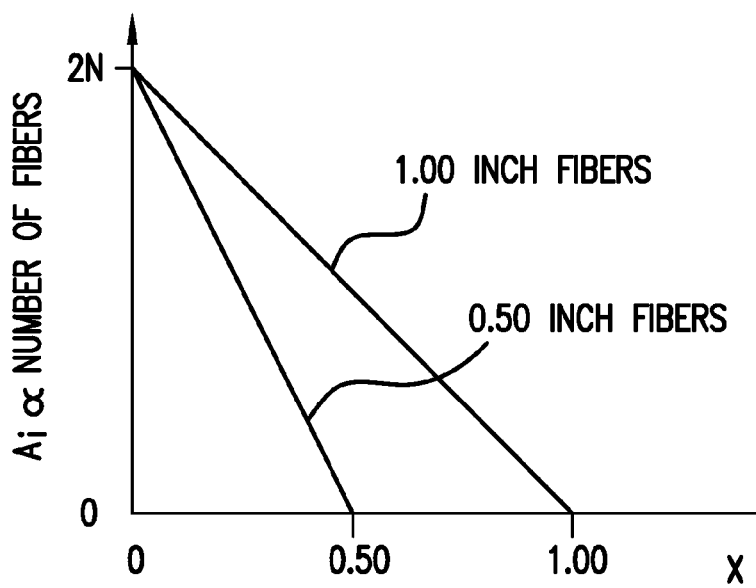
FIG. 7A shows two ideal fibrograms for monodisperse, or monolength, fiber length distributions.

FIG. 7A shows two ideal fibrograms for monodisperse, or monolength, fiber length distributions, having N fibers of all 0.5 inch or 1.00 inch length. (This does not mean that all fibers simply extend 0.5 inch or 1.00 inch from the needles, because the fibers are looped around and are locked to the needles. The needles engage the individual fibers at random distances along the fiber, and the two ends of each individual fiber can be at any distance from the needles.) More specifically, the ideal $A_i$ are seen to be proportional to the number of fibers in the tapered beard along the scan line 164 (across the tapered beard) at each distance x. Thus the ideal fibrogram for monodisperse (or monolength hereinafter) fiber length distributions consisting of all 0.5 inch fibers starts at 2N at x=0 and falls linearly to 0 at x=0.5 inch. Similarly, the ideal fibrogram for a monolength distribution having N identical 1.0-inch fibers starts at 2N at x=0 and falls linearly to 0 at x=1 inch.

In FIG. 7A, $A_i$ peaks at 2N (two times the number of fibers) at x=0 because each fiber loops around the sampler needles 142 and 144 and accordingly has two segments extending from the needles 142 and 144. The reason for the linear behavior follows from the assumption of random sampling along the length of each fiber by the needle sampler. One end of the fiber is first "seen" as x decreases until the other end is seen. Methods embodying the invention for calculations of fiber properties from fibrograms thus build on Hertel's pioneering work, with important aspects of the invention being particularly the image-based apparatus and methods, the elastomer lock sampler, and the extensions to rigorous calibration for PDFs described next.

Figure 7B:
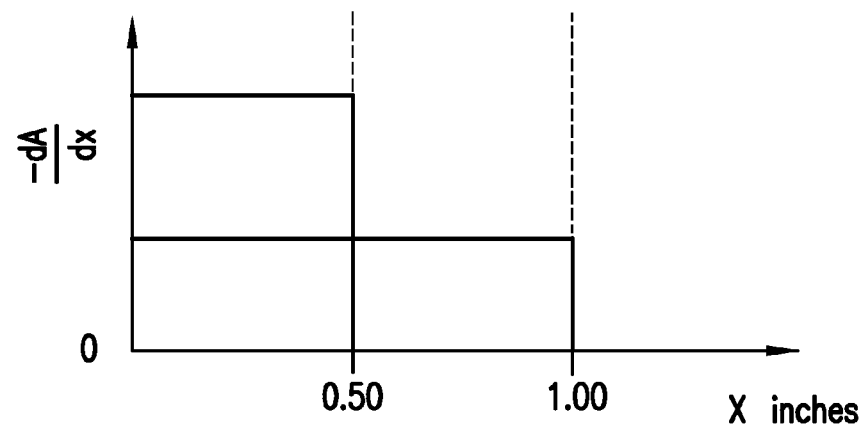
FIGS. 7B and 7C are plots of the negative first derivatives and the negative second derivatives of the FIG. 7A fibrograms.
Figure 7C:
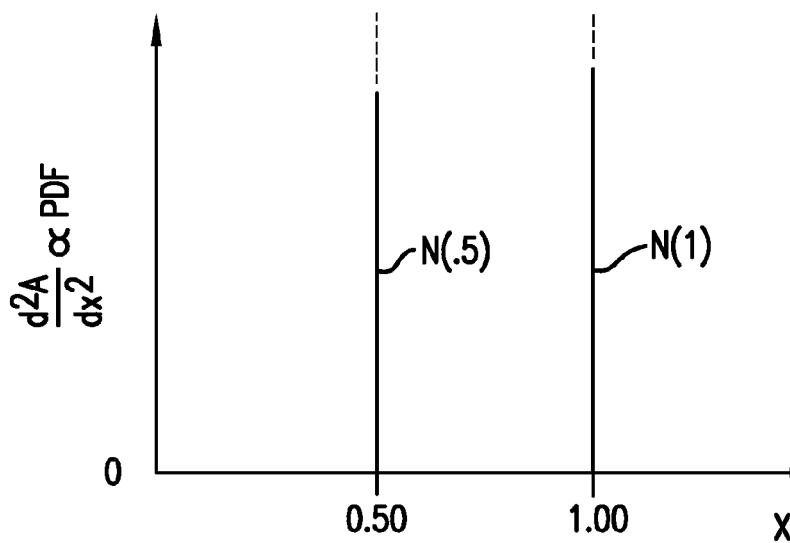

Referring now to FIGS. 7B and 7C, the negative first derivative, $$-\frac{dA_i}{dx},$$

and negative second derivative $$-\frac{d}{dx}\left[-\frac{dA_i}{dx}\right] = \frac{d^2 A_i}{dx^2}$$

are plotted, which are based on the assumption above of random sampling along the length of each fiber for ideal fibrograms shown for monolength 0.5 inch and 1.0 inch samples. It is particularly seen in FIG. 7C that $$\frac{d^2 A_i}{dx^2}$$

yields a Dirac delta function at x=0.5 in, for the fibrogram based on 0.5-inch fibers, and another delta function at x=1.00 inch for the fibrogram based on 1.0-inch fibers. These second derivatives are evidently the appropriate PDFs for monolength fiber length distributions. The results of this example can, of course, be generalized to an arbitrarily larger number of monolength groups and to relatively narrow ranges of fiber lengths. Using a slightly different analytical approach, Hertel discovered this relationship in the 1940s.

Attempts to double differentiate cotton fibrograms to produce PDFs have been heretofore unsuccessful because of errors and noise in the amount vs x, or fibrogram, curves, because of poor spatial and spectral resolutions, and because of non-ideal A vs x responses, such as the peaking phenomena described above, or because of other non-ideal responses. No commercially available instruments have heretofore been known which provide all of the required LFC and SFC data products from tapered beards. This is why the senior inventor herein led the development of the AFIS method in the 1980s (again, for an example see the disclosure of Shofner et al U.S. Pat. No. 5,270,787 titled "Electro-Optical Methods and Apparatus for High Speed, Multivariate Measurement Of Individual Entities In Fiber Or Other Samples") to provide PDFs from which all useful data products could be generated. AFIS has become a reference method for some fiber length data products, notably SFC. However, the aggressive opening device used in AFIS is known to produce fiber breakage, thus artificially increasing SFC and also decreasing LFC data products. The instant invention provides improvements with respect to breakage. The methods and apparatus of the subject invention also have the potential to become a reference method. Subject invention is thus a second visit for the senior inventor to the important task of providing improved fiber length measurements for commerce.

It shall now be shown how double differentiation of corrected or calibrated A vs x responses enables direct determination of calibrated PDFs. That is, the method enables correction for non-ideal measurement issues, one of which, the peaking phenomenon, is discussed hereinabove. It will be appreciated that these methods apply to amount versus distance Fibrograms resulting from air flow ($L_a$), optical extinction ($L_O$) and to the instant image-based $L_i$. Experimental results reported hereinbelow for $L_i$ confirm the performance.

Again, the fibrograms shown in FIG. 6 are real world fibrograms for polydisperse, i.e., polylength PDFs, for cotton; and the ideal figrograms in FIG. 7A are idealized responses for monolength PDFs. Particularly noteworthy in FIG. 6 are the peaking behavior already discussed and the extrapolated responses 240, 242 and 244 for distances x less than $x_p$. Also of note in FIG. 6 is that the actual responses 246 for distances x less than $x_p$ are substantially identical for all three samples, whereas the extrapolated responses 240, 242 and 24 are not.

Figure 8:
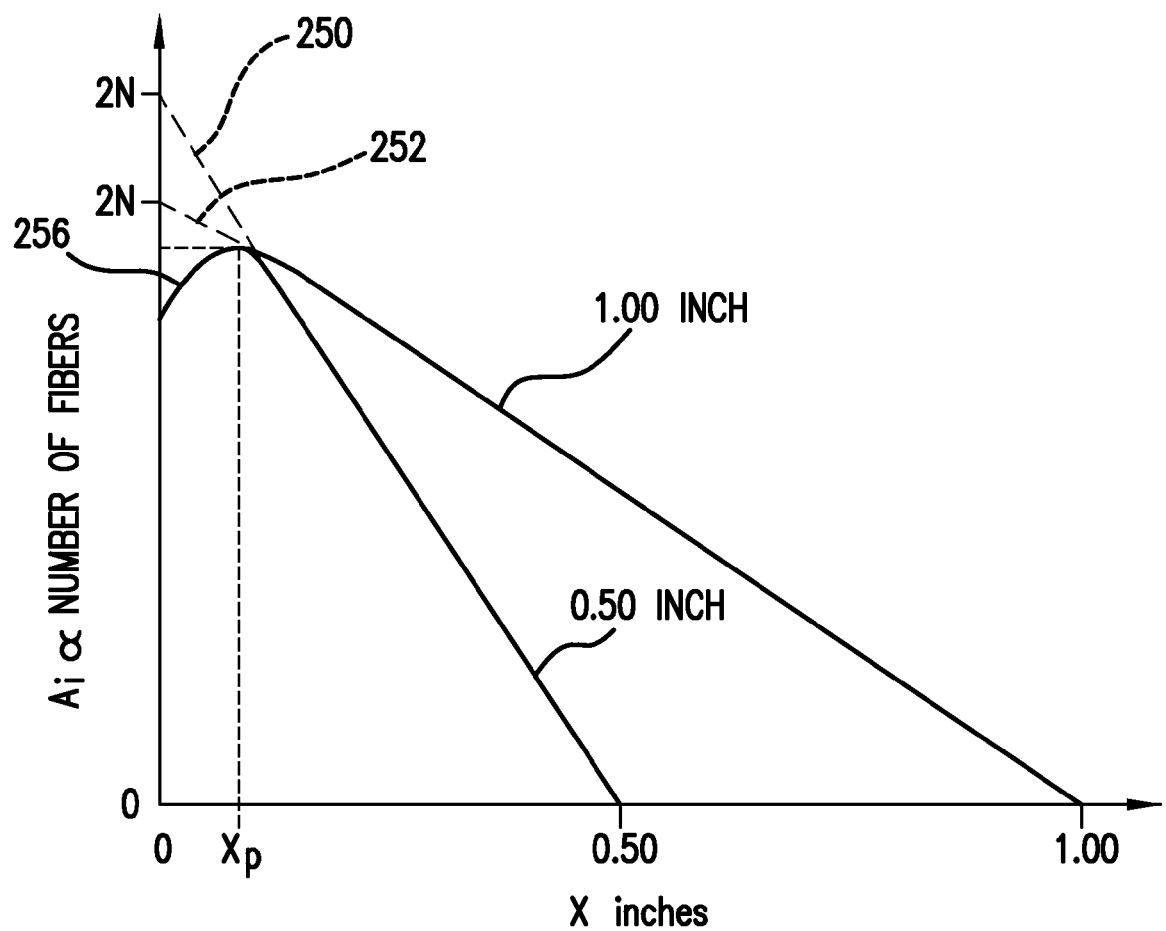
FIG. 8 is a real-world fibrogram for monolength PDFs.

FIG. 8 shows real world fibrograms for two monolength fiber groups of 0.5 and 1.0 inch, and which differ from the idealized fibrograms of FIG. 7A primarily by the real world peaking response 256 near $x_p$. Again it is seen that the extrapolated responses 250 and 252 are different and the actual responses 256 for distances x less than $x_p$ are substantially the same, for each length group. Extrapolated total responses 250,252, from x=0 to x=0.5 or 1.0 inches, are thus the corrected or ideal responses for the known monolength fibers. It follows that step-wise or sequential application of such correction procedures leads to a overall correction of the A vs x response, thus producing a calibrated amount verus distance response, from which double differentiation methods can yield all desired data products. Further, traditional methods may be advantageously applied to such calibrated amount verus distance responses.

Three steps of a calibration procedure, for amounts by number and resultant PDFs by number (from which PDF by weight and all by number or by weight statistics can be determined) are as follows:

1. A plurality of known monolength fiber distributions are first tested to establish the actual $A_i$ vs x responses, as shown in FIG. 8 for two such monolength groups, a first, longer length group L1=1.00 inch and a second, shorter length group L2=0.50 inch. The fibers should have generally the same diameters and compositions as unknown polylength fibers to be tested later. The number of monolength groups may be increased as required for precision and accuracy.

2. The actual $A_i$ vs x fibrograms for the known length monolength groups are compared to the ideal case (e.g. FIG. 7A), which intersects the x axis at the monolength and the $A_i$ axis at 2N. The comparisons are preferably by linear regression techniques which yield, for each monolength group, x and y axis intercepts at the known lengths and at 2N, respectively, and linear responses therebetween. Other "best-fit" or even graphical techniques may also be employed.

3. Correction functions are developed for each of the plurality of such monolength inputs. For example, a multiplicative correction is applied to correct the actual $A_i$ to ideal linearity and to intersections at x=L of the known monolength group length and 2N for the amount. In the example of FIG. 8, only one non-ideal response phenomenon, peaking near xp, is corrected and the correction function is simply an extrapolation. Other non-ideal responses may be so corrected or calibrated.

These sequential procedures or steps, most of which can be automated, are repeated for typically five monolength groups. Useful but approximate results can be obtained with one monolength group; higher accuracy and precison result with ten or more groups but at the expense of time for the calibrations. The procedures are also applicable to calibration in terms of linear densities or tex. This correction function procedure is quite general; it is not limited to peak correction.

Execution of Calibration Steps 1-3 completes the basic calibration procedure. Corrected or calibrated $A_i$ vs x curves for the selected number of monolength groups are stored as arrays in the computer memory. Interpolations from the relatively small plurality of monolength fiber groups are also developed and stored. Application to and analyses of these results to unknown fiber length distributions follows from these basic calibration steps. It will be seen that the analytical steps are also three in number, with numerous sub-steps.

Figure 9A:
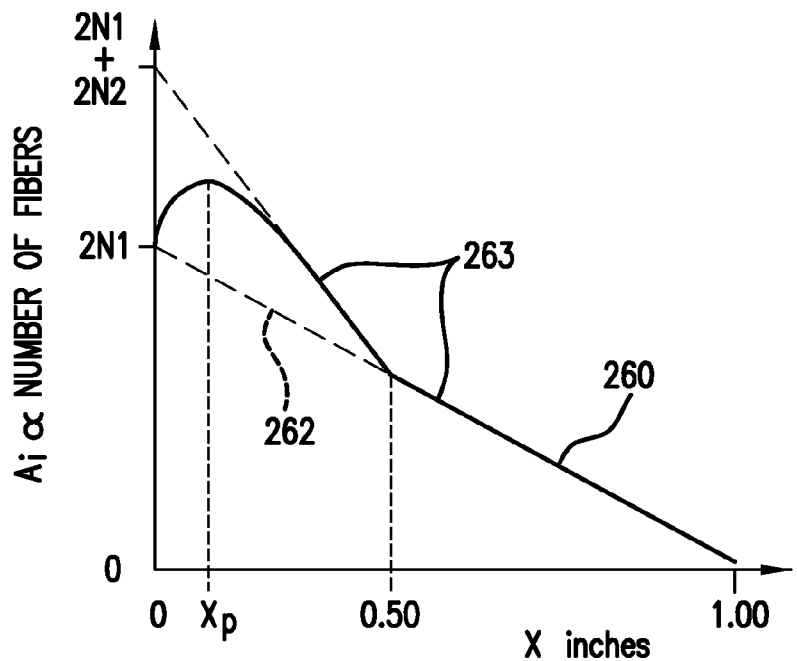
FIGS. 9A, 9B and 9C are plots illustrating how calibrated, corrected $A_i$ responses are used for unknown samples under test.
Figure 9B:
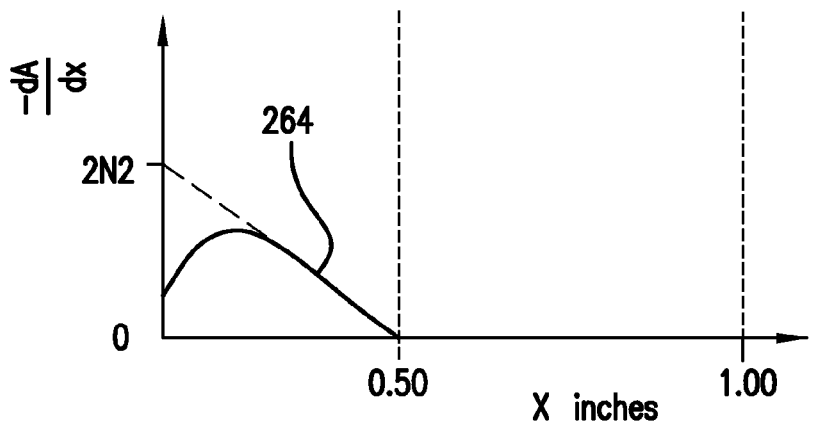
Figure 9C:
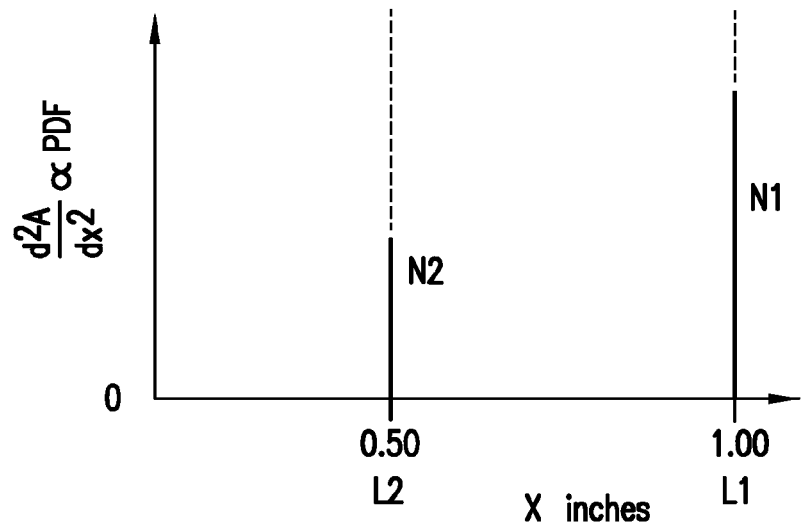

FIGS. 9A, 9B and 9C illustrate how these calibrated, corrected $A_i$ responses are used for unknown samples under test. For illustrative example, we again use for clarity two monolength groups with N2 0.5-inch and N1 1.0-inch fibers, to confirm the validity of the procedure. FIG. 9A shows the actual, non-ideal $A_i$ vs x response 260, in which the peak at $x_p$ and break in slope at x=0.5 are seen in the solid line 260.

There are three primary steps in the analysis. The first step is correction of the actual response versus distance response and that primary step is comprised of several sub-steps, as follows. In the first sub-step of analysis, a longest length group L1 is selected, in this example, 1.00 inch. Since it is known that this length group causes a linear response, when corrected, the calibrated response is extrapolated to x=0 and the number of fibers in that group, N1, is determined from the known or calibrated 2N1 intersection for this L1 group. The corrected response 262 for this first length group is thus the entire linear response from (0, 2N1) to (1, 0). Note that group does not necessarily mean a single or monolength group but a range of fiber lengths.

In the next sub-step, in these sequential steps of analysis, all of which are executed by a computer program executing in CPU 186, the total corrected and extrapolated curve 262 for the longest length group L1 is subtracted from the total measured curve 260, yielding the response curve 264 of FIG. 9B. This response corresponds to the remaining fiber lengths (in this example, one), with the longest group (or groups) removed or subtracted out. The extrapolation procedure is repeated for this next-longest length group L2, thus providing the number of fibers N2 in that group of length L2, from the linear extrapolation to 2N2 at x=0.

These first sub-steps are repeated until the complete range of fiber lengths observed is covered. Again, the number of such sub-steps depends on the accuracy and precision required. Ten such sub-steps are usually adequate for cotton.

The second primary step is to apply the sequentially-subtracted and corrected monolength calibration results to the actual response 260 to produce total corrected or calibrated response 263 (FIG. 9A) This is accomplished by adding or superposing the individual responses from the plurality of sub-steps in primary step one.

Third, and finally, this calibrated $A_i$ vs x response 263 may now be analyzed with traditional methods or by double differentiation.

To now complete the two component example, FIG. 9 confirms the validity of the method, using double differentiation of the calibrated or corrected $A_i$ vs x response 263 in FIG. 9A: the composite PDF by number is seen in FIG. 9C to be the expected bimodal fiber length distribution, with N1 fibers at L1 and N2 fibers at L2.

Like the calibration procedures disclosed above, these monolength calibration and sequential substraction test and analysis procedures can be generalized to any number of length groups or applied to linear densities or tex responses. Significantly, carefully-executed calibrations with a few known monolength groups can enable a larger number of analytical result groups by interpolations, all performed by software executing in CPU 186.

Results

Figure 10:
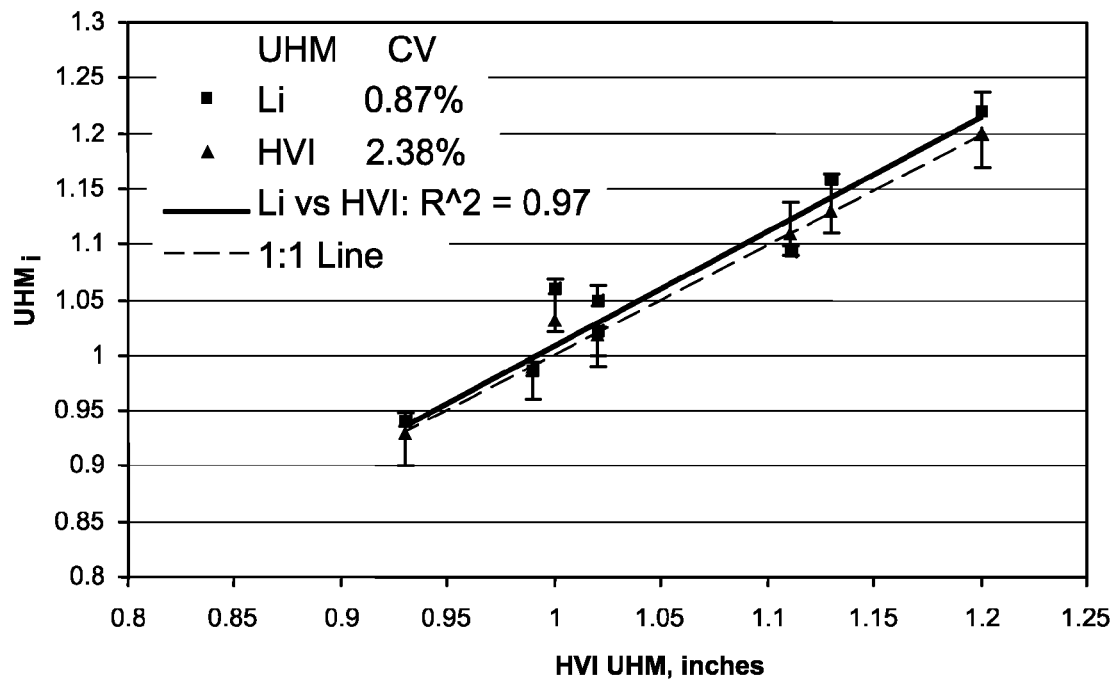
FIG. 10 shows plots of UHMi versus UHM HVI.

The following results are for staple standard materials provided by USDA/AMS, Memphis, Tenn. FIG. 10 shows $UHM_i$ from prototype image-based length measurement apparatus embodying the invention, $L_i$, versus HVI UHM, including half error bars of one standard deviation, for clarity. Average CVs are shown in the inset on FIG. 10. Evidently, $L_i$ performance, as measured by average CVs, is superior to that of the particular HVI used for these comparisons to produce the corresponding LFC data. This surprising and most favorable result appears to be generally valid.

The data shown in FIG. 10 are based on traditional analyses (i.e., Hertel's methods) and thus rely on calibration cottons. True $UHM_i$ data products, that is, UHMs derived directly from uncalibrated PDFs, were produced but did not agree as well with HVI as the more traditional analysis. Calibrated PDF results are not available for these tests. Further investigations are required to explain why the raw PDF-based and traditional LFC data products differ and to confirm if the disclosed PDF calibration method are better.

The linear regression line is not coincident with the HVI 1:1 line. This is because the $L_i$ apparatus and HVI apparatus were calibrated on a different set of calibration cottons in different laboratories.

Figure 11:
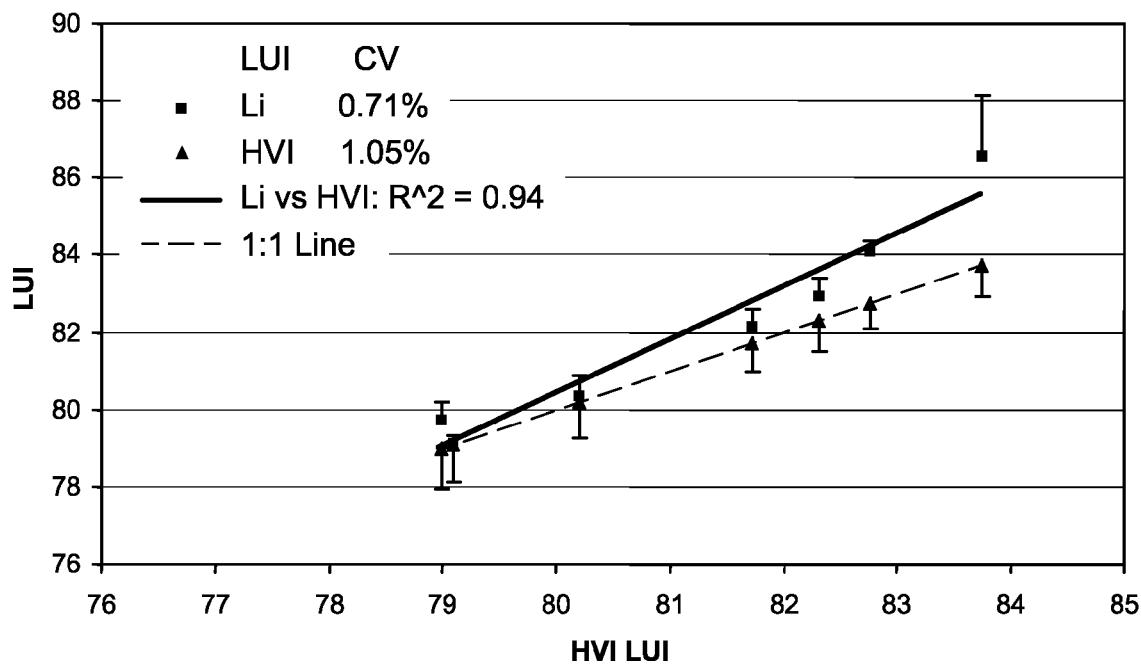
FIG. 11 shows plots of True LUIi versus LUI HVI.

FIG. 11 shows PDF-based $LUI_i$ versus HVI LUI. PDF-based $LUI_i$ means that LUI was derived directly from the raw PDFs, using the double differentiation procedures above and using the basic definitions for LUI=ML/UHM, and without any use whatsoever of calibration cottons. Again we observed superior performance, based on average CVs. We also note the level difference in the two completely different methods for LFC data products. This observation is relevant to the investigation into UHM differences just mentioned.

Figure 12:
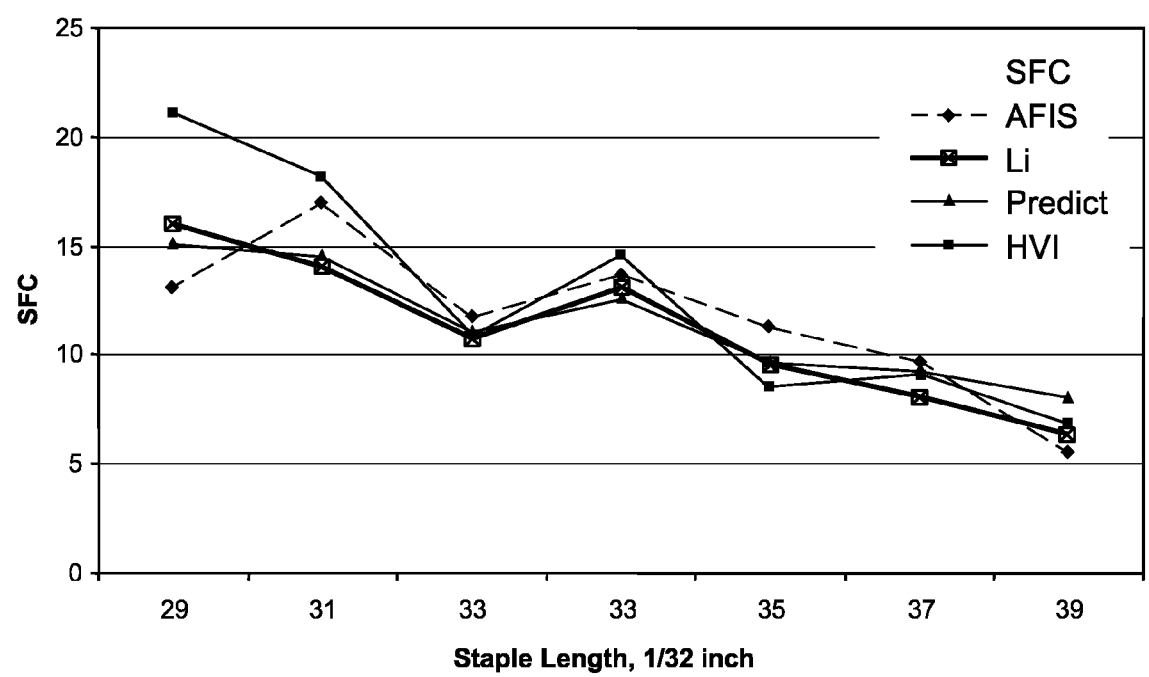
FIG. 12 shows SFC for USDA/AMS Staple Standards by four independent methods.

FIG. 12 shows SFC for the USDA/AMS Staple Standards by four independent methods: Li methods embodying the subject invention, by HVI, by AFIS, and from a prediction equation based on UHM and LUI (from HVI or $L_i$) and developed by Knowlton et al, USDA/AMS, Memphis, Tenn. AFIS may be regarded as a reference method for SFC and the methods embodying the subject invention as a candidate reference method. It is important to note that the AFIS and $L_i$ methods are based on completely different scientific principles and are therefore entirely independent of each other. The $L_i$ SFC data reported are independent of any calibration cottons whatsoever. Further, the raw PDFs are seen to yield quite satisfactory results, without the rigorous calibration procedures enabled by the invention. The fact that the $L_i$ and AFIS or AFIS-based SFC(w) levels are so close to each other is truly remarkable. As noted above, the $L_i$ method has the potential to become a reference method for SFC and for LFC data products, particularly when the rigorous calibration procedures of the invention are applied.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. Apparatus for fiber length measurements from a tapered beard attached to a fiber sampler, comprising:
   a rectangular channel into which a tapered beard is drawn by a gas flow through said channel, said channel having two opposed major sides corresponding to channel width and length, and two opposed minor sides corresponding to channel height and length;
   one of said major sides comprising a transparent window;
   an optical imaging device viewing the tapered beard through said transparent window for acquiring a two-dimensional image of the tapered beard; and
   a digital computer connected to an output of said optical imaging device for storing two-dimensional image data and determining fiber amount as a function of one-dimensional distance x from the fiber sampler by averaging across the width of the tapered beard as imaged.

2. The apparatus of claim 1, wherein said optical imaging device comprises a scanner intended for scanning documents.

3. The apparatus of claim 2, wherein said scanner is a color scanner.

4. The apparatus of claim 2, wherein said scanner includes an illumination source.

5. The apparatus of claim 1, wherein said optical imaging device comprises a digital camera.

6. The apparatus of claim 1, wherein said rectangular channel has a height of approximately 2 mm, a width of approximately 100 mm, and a length of approximately 50 mm.

7. The apparatus of claim 6, wherein gas flows through said channel at a rate of approximately 0.25 m$^3$/sec.

8. The apparatus of claim 1, wherein said optical imaging device provides spectrally-resolved data, and fiber amount as a function of one-dimensional distance x is determined based on data for a particular color.

9. Apparatus for fiber length measurements from a tapered beard attached to a fiber sampler, comprising a scanner intended for scanning documents positioned with reference to the tapered beard for acquiring a two-dimensional image of the tapered beard.

10. The apparatus of claim 9, which further comprises a digital computer connected to an output of said scanner for storing two-dimensional image data and determining fiber amount as a function of one-dimensional distance x from the fiber sampler by averaging across the width of the tapered beard as imaged.

11. The apparatus of claim 10, wherein said scanner provides spectrally-resolved data, and fiber amount as a function of one-dimensional distance x is determined based on data for a particular color.

12. A method for image-based length measurement comprising:
   acquiring a two-dimensional digital image of a tapered beard of fibers, the beard having a length;
   employing a computer to analyze the digital image to determine fiber amount as a function of one-dimensional distance along the length of the tapered beard by averaging across the width of the tapered beard as imaged; and
   analyzing the determined fiber amount as a function of distance to produce a fiber length distribution.

13. The method of claim 12, which comprises acquiring spectrally-resolved image data, and employing the computer to determine fiber amount as a function of one-dimensional distance based on data for a particular color.

* * * * *